United States Patent [19]

Thomas et al.

[11] Patent Number: 4,968,144
[45] Date of Patent: Nov. 6, 1990

[54] SINGLE BEAM AC INTERFEROMETER

[75] Inventors: Robert L. Thomas, Huntington Woods; Pao-Kuang Kuo, Troy; Lawrence D. Favro, Huntington Woods, all of Mich.

[73] Assignee: Wayne State University, Detroit, Mich.

[21] Appl. No.: 321,103

[22] Filed: Mar. 9, 1989

[51] Int. Cl.⁵ ............................................. G01B 9/02
[52] U.S. Cl. .................................... 356/354; 356/432
[58] Field of Search ............... 356/354, 355, 356, 357, 356/359, 360, 432

[56] References Cited

U.S. PATENT DOCUMENTS

| | | | |
|---|---|---|---|
| 4,522,510 | 6/1985 | Rosencwaig et al. | 356/432 X |
| 4,581,939 | 4/1986 | Takahashi | 356/432 X |
| 4,652,757 | 3/1987 | Carver | 356/432 X |
| 4,750,822 | 6/1988 | Rosencwaig et al. | 356/432 X |
| 4,790,664 | 12/1988 | Saito et al. | 356/432 |

Primary Examiner—Davis L. Willis
Assistant Examiner—Matthew W. Koren
Attorney, Agent, or Firm—Reising, Ethington, Barnard, Perry & Milton

[57] ABSTRACT

A single beam interferometer (10) comprises an intensity modulated laser beam (16) having a focus area for heating a test area (18) on the surface of a sample (12) producing a thermal bump (20). An unfocused probe laser beam (30) is directed toward the solid at an angle and has a beam area greater than the focus area of the heating beam (16). The sample (12) has a reflective surface for reflecting the probe beam (30). The reflected beam (31) comprises an AC beam portion (32) refracted by the thermal bump (20) and a DC beam portion (34) reflected off the unheated surface of the sample (12). The interference pattern (36) produced by the reflected beam (31) is detected and processed to obtain optical, elastic and thermal parameters of the sample (12).

17 Claims, 1 Drawing Sheet

SINGLE BEAM AC INTERFEROMETER

TECHNICAL FIELD

The invention relates to an interferometer for measuring optical, elastic and thermal parameters of a solid through non-destructive testing.

BACKGROUND OF THE INVENTION

Recently, several interferometeric techniques have been developed to measure ultrasonic, photo acoustic and photo thermal displacement in non-destructive testing. The ability to focus a very small area gives high spatial resolution. Generally two types of interferometeric techniques have been used in ultrasonic and photo thermal displacement detection. One such technique is the classical Michelson interferometer, and a second is based on a doppler shift of the frequency of the reflected or scattered light, caused by surface oscillations and its demodulation by an interferometer. This scheme is sensitive to surface velocity.

The Michelson interferometer is very common in intereferometry and disclosed in R.S. Sharpe, ed. *Research Techniques in NDT*, vol. VII, p. 267. The incident laser beam is split into two components by a beam splitter The first component is deflected by 90 degrees by the beam splitter constituting the reference beam. This reference beam is reflected from a plane mirror and retraces its path to the beam splitter and passes undeflected therethrough. The second component passes through the beam splitter undeflected and constitutes the probe beam. This probe beam is reflected off the sample surface and retraces the path back to the beam splitter, where it is deflected by 90 degrees. The two reflected beams are recombined at the beam splitter and travel together to the detector. Since both beams originate from the same coherent source, interference fringes are formed at the detector which are determined by the optical path difference of the two beams. Each fringe corresponds to a displacement of the quarter of the wave length of light. The fringe intensity varies sinusoidally as a function of optical path difference. The Michelson interferometer is not suitable to measure displacements much less than a wave length The noise introduced by mechanical and thermal fluctuations causes the relative path length to fluctuate It is generally very sensitive to air currents and vibrations.

Another interferometeric technique which detects ultrasonic motion uses wavelength transmission selectivity of the Fabry-Perot interferometer to detect the wavelength changes due to Doppler shift. The sample surface is illuminated by a frequency-stablized laser and the reflected and scattered light is collected by a telephoto lens. This light is received by a confocal Fabry-Perot interferometer which optimizes the light gathering power and illuminates only the central fringe. The change in wavelength is proportional to the surface displacement velocity. A Wollaston prism is used to split the beam. This makes both the reference and probe beam equal One of the two beams is focused onto an undisturbed portion of the sample and serves as the reference The other beam is focused onto a position of the sample surface periodically heated. The surface displacement due to thermal expansion causes phase modulation of this beam. Both beams reflected from the sample recombine in the Wollaston prism and interfere on a photo-detector. J.T. Fanton and G.S. Kino, Appl. Phy. Lett. 51, p. 66 (1987).

Other non-interferometric systems have been developed to detect the "thermal bump". In this scheme, the sample is heated by a focused modulated pump beam, creating a periodic displacement "thermal bump" due to thermal expansion. A focused probe beam is reflected off the bump. The deflection of the reflected probe beam, which is proportional to the slope of the bump is measured. The heating beam is obtained from an Ar+ ion laser, which is intensity modulated using an accoustic-optical modulator. The beam is spatially filtered and expanded using a beam expander. Then it is reflected off a plane front surface mirror, which is mounted on a rotating stage and focused onto the sample using a microscope objective. Since the mirror is mounted off axis on the stage, the angle of incidence of the beam on the focusing lens is changed without moving away from the lens. The heated spot and hence the bump, can be scanned relative to the probe beam spot by turning the rotating stage. The probe beam is obtained from an He-Ne laser, which is spatially filtered and expanded using a beam expander. The axis of polarization of the laser is rotated by turning the laser head, in order for the beam to pass through the polarizing beam splitter It passes through a quarter wave plate and reflects off a dichroic mirror onto the same microscope objective, which focuses both beams on the sample. The probe beam is reflected from the sample, passes through the same path and arrives at the beam spliter with the axis of polarization rotated by 90 degrees. The signal is obtained from electrodes at each edge of the square cell. The deflection of the beam in two perpendicular directions is measured by taking the difference signals electronically, from the electrodes on either side. The signal is detected synchronously with the modulation of the bump using a lock-in amplifier. The optical reflectively change is also measured by taking the sum of all four electrodes. The problem with this type of technique is that it is also very sensitive to air currents and vibration. Such system is disclosed by A. Rosencwaig, J. Opsal and D.L. Willenborg, Applied Physics Lett. 43, 166 (1983).

SUMMARY OF THE INVENTION AND ADVANTAGES

The invention is an interferometer assembly for measuring optical and thermal parameters of a sample. The assembly comprises heating means for producing a thermal bump at a test area on the sample, the heating means (14) having a focus area at the test area; probe means for producing a probe laser beam having a probe area greater than the focus area and directed toward the test area; and control means responsive to the reflected probe laser beam reflected from test area for measuring interference pattern of the reflected probe laser beam caused by the thermal bump.

The advantages of this assembly include non-sensitivity to fluctuations in air currents or mechanical vibrations. Any external influence will uniformly affect the probe beam.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
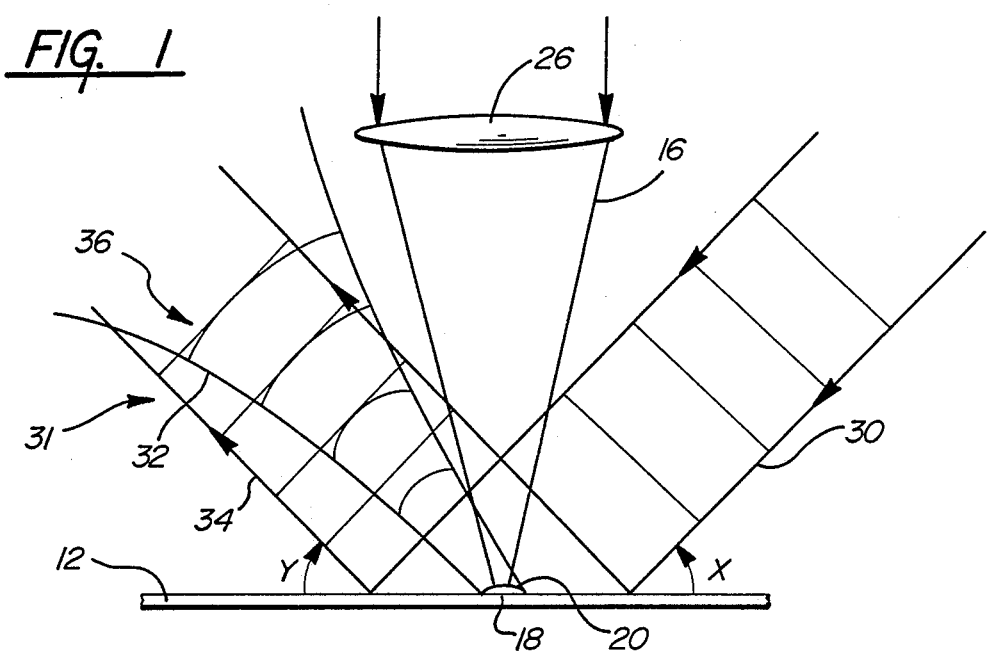
FIG. 1 is a schematic diagram of the subject invention.
Figure 2:
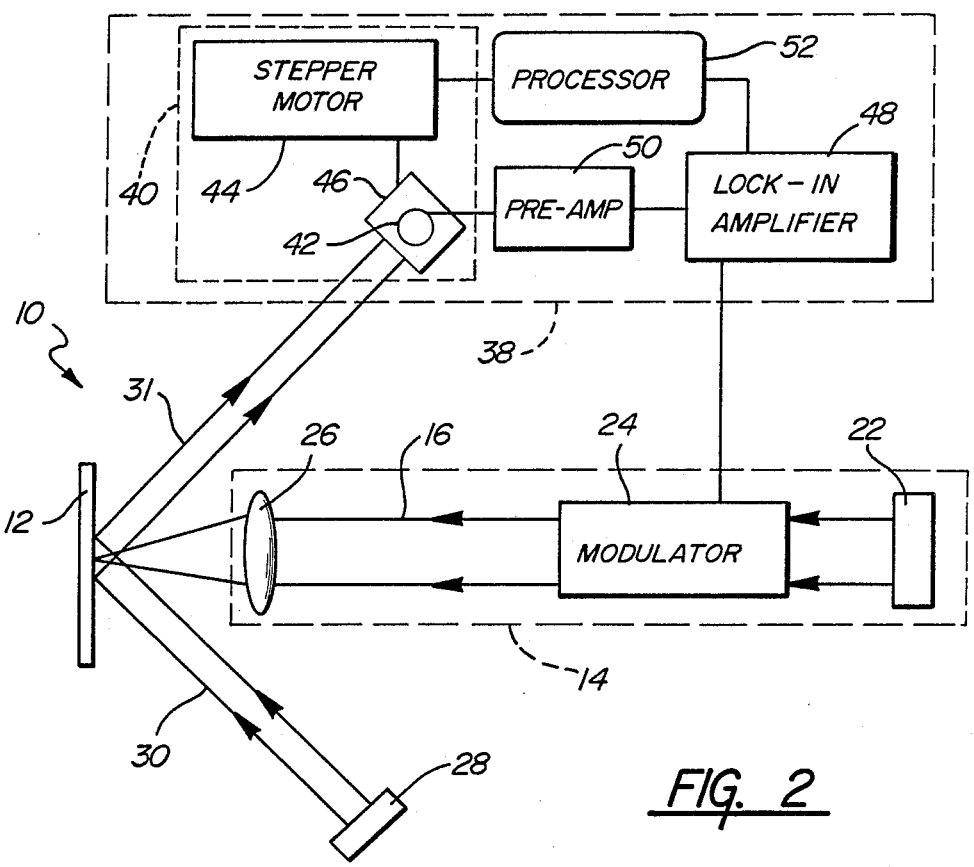
FIG. 2 is a diagram of the incident laser beams and reflected interfered laser beam.

A single beam interferometer assembly for measuring optical, elastic and thermal parameters of a solid surface or sample 12 is generally at 10 in FIG. 1.

The assembly 10 includes heating means 14 for producing a heating laser beam 16 directed toward the surface of the sample 12 at a test area 18. The heating laser beam 16 has a focus area at the surface on the sample 12. A time dependent "thermal bump" 20 is produced on the surface of the sample 12 by the heating means 14.

The heating means 14 includes an Argon ion laser 22. The heating means 14 further includes modulator means 24 for receiving the Argon ion laser 22 and producing an intensity modulated laser beam 16. The modulator means 24 is generally an acoustic-optic modulator The heating means 14 also includes focusing means 26 for focusing the intensity modulated laser beam 16 to the focus area of approximately a ten micrometer spot at the test area 18 on the surface 12. The focusing means 26 may be a lens as commonly known. The average incident power at the surface 12 is kept less than the damage threshold of the material, typically less than about 40 milliwatts. The heating laser beam 16 is directed perpendicular or 90° to the solid 12.

The assembly 10 also includes probe means 28 for producing a probe laser beam 30 having a probe area greater than the focus area of the focused heating laser beam 16. The probe laser beam 30 is directed toward the test area 18. The probe means 28 is a 3 mW He—Ne laser producing a 6328 Angstrom beam 30. The probe laser beam 30 is directed toward the surface 12 at an angle X, which is less than 90°. The probe beam 30 is not focused and has a spot diameter or area of approximately 800 micrometers at the sample 12. Therefore, the heating beam 16 spot can be laterally displaced with respect to the center of the probe beam 30 by moving the focusing lens 26. The probe laser beam 30, being larger than the size of a thermally induced bump 20, is reflected from the surface of the solid 12.

The information of the thermal bump 20 is contained in the distortion or interference pattern of the reflected wave front caused by the bump 20. The reflected laser beam 31 is reflected off the surface of the sample 12 at an angle Y, equal to the angle X. A time dependent optical intensity pattern is produced by the superposition of the diffracted AC wave front 32 from the bump 20 and the reflected undistorted DC wave front 34 from the surrounding surface 12. The interference 36 between the spherical 32 and planar 34 wave fronts gives rise to the traditional pattern of Newton's rings. Due to the small size of both the bump 20 and the probe beam 28, only two or three of the rings are visible at experimetally convenient distances. The resulting time dependent interference pattern 36 contains information about the thermal, optical and elastic properties of the sample 12. Since only a single beam 30 is used, noise from mechanical vibration and fluctuations and air currents is greatly reduced.

The assembly 10 includes control means 38 for receiving the reflected probe beam 31 comprising the AC 32 and DC 34 wave fronts off the test area 18 for measuring the interference pattern of the reflected probe beam 31, which represents parameters of the solid 12. The control means 38 includes scanner means 40 for scanning the reflected beam 31 for measuring the wave pattern of interference. More particularly, the scanner means 40 includes detector means 42 for detecting a portion of the reflected beam 31, and driver means 44 for moving the detector means 42 across the area of the reflected beam 31. The detector means 42 is generally a photodiode which is large enough to capture the entire probe. The diode 42 detects the radiant energy of the reflected beam 31 and produces a detection signal representative of the magnitude of the sensed energy. A slit assembly 46 is placed in front of the diode 42 to detect only a portion of the reflected beam 31. The driver means 44 is generally a stepper motor controller for moving the detector or photodiode 42 along the reflected beam 31. In other words, the detector/slit assembly 42, 46 is scanned across the reflected beam 31 using the stepper motor 44 while recording the interference pattern.

Alternatively, the scanner means 40 may be a detector array of diodes in place of the single scanned detector 42, 44. Such an array would increase the data acquisition speed. The detector array includes an array of detectors spaced along the area of the reflected probe beam.

The control means 38 includes a lock-in amplifier 48 for detecting the reflected beam 31 synchronously with the modulated heating laser 22. Lock-in amplifiers 48 are well known in the art for synchronous detection of a weak signal. The detection signal from the detector 42 is synchronously detected by the lock-in amplifier 48. In other words, the amplified detection signal is sent to the lock-in amplifier 48. The lock-in amplifier 48 samples the detection signal at a time synchronous to the modulated heating laser 22. The control means 38 also includes pre-amplifier means 50 for amplifying the detection signal.

The assembly 10 includes an information or data processor 52 for receiving the sampled or data signal measuring the interference pattern of the reflected probe beam 31 and to produce an output indicative of parameters of the sample 12. The data received by the processor means 52 from the lock-in amplifier 48 is synchronized with the modulated heating laser 22. The processor 52 also controls the stepper motor 44 for scanning the wavefront, as previously discussed. The processor 52 is generally a computer, microprocessor, or the like, having analysis capabilities. The detailed knowledge of the probe beam's 30 characteristics is essential in the quantitative analysis of the data. The processor 52 determines the position and magnitude of the Gaussian beam waist by measuring the beam 31 profile at several distances with a chopped probe beam 30.

The processor 52 obtains the information about the interference pattern 36. Traditional fringe counting methods may be too imprecise. A least-square fit scheme of the measured data to a theoretical calculation of the fringe pattern based on the detailed shape and time variations of the thermal bump 20 may be used. Using a least-squares fit routine, the optical reflectively change and the size and height of the bump can be obtained from the fits. The interference pattern is essentially a holograph of the thermal bump 20. In principle, the complete interference pattern 36 is recorded experimentally and a holographic reconstruction of the bump 20 is possible This interferometer 10 has been tested and used on a silicon wafer and is able to obtain a signal with a one second time constant with a heating beam 16 power as low as 0.1 mW. This corresponds to a bump 20 height of approximately $10^{-3}$ Angstrom at 1 kHz.

The subject interferometer 10 has proven quite good in sensitivity. A single unfocused laser beam 30 is used and there are no optical components between the laser 28 and the detector 42. The surfaces 12 must be reflective.

Also included is a method of measuring optical and thermal parameters of a sample. The method including the steps of heating a test area of a sample producing a thermal bump, directing a probe laser beam having a beam area greater than the test area toward the test area, detecting the reflected laser beam off the test area, measuring the interference pattern of the reflected laser beam wherein the optical and thermal parameters of the sample are obtained from the interference pattern. Further included are the steps of heating the test area by a heating laser beam directed perpendicular to the sample, directing the probe laser beam at an angle less than 90° toward the test area, scanning the reflected laser beam to measure the wave pattern of interference and producing a detection signal, intensity modulating the heating laser beam and focusing the modulated beam to the test area, and synchronizing the detecting with the modulating.

The invention has been described in an illustrative manner, and it is to be understood that the terminology which has been used is intended to be in the nature of words of description rather than of limitation.

Obviously, many modifications and variations of the present invention are possible in light of the above teachings It is, therefore, to be understood that within the scope of the appended claims wherein reference numerals are merely for convenience and are not to be in any way limiting, the invention may be practiced otherwise than as specifically described.

What is claimed is:

1. An interferometer assembly for measuring optical and thermal parameters of a solid surface of a sample, said assembly comprising; heating means (14) for producing a thermal bump (20) at a test point on the sample (12), said heating means (14) having a focus area at the surface of the sample (12); probe means (28) for producing a probe laser beam (30) directed toward the test area and having a probe area greater than said focus area; and control means (38) responsive to the reflected probe laser beam (31) reflected from the test area (18) for measuring interference pattern of the reflected probe beam (31) caused by the thermal bump (20).

2. An assembly as set forth in claim 1 further characterized by said heating means (14) producing a heating laser beam (16) directed toward the test area.

3. An assembly as set forth in claim 2 further characterized by said control means, (38) including scanner means (40) for scanning the reflected beam (31) to measure the interference pattern and for producing a detection signal 4. An assembly as set forth in claim 3 further characterized by said heating means (14) including modulator means (24) for producing an intensity modulated laser beam (16).

5. An assembly as set forth in claim 4 further characterized by said heating means including focus means (26) for focusing said intensity modulated laser to said focus area.

6. An assembly as set forth in claim 5 further characterized by said scanner means (40) including detector means (42) for detecting a portion of said reflected beam to produce said detection signal.

7. An assembly as set forth in claim 6 further characterized by said scanner means (40) including driver means (44) for moving said detector means (42) across the area of said reflected beam (31).

8. An assembly as set forth in claim 7 further characterized by said control means (38) including a lock-in amplifier means (48) for detecting said reflected beam (31) synchronously with said modulator means (24).

9. An assembly as set forth in claim 8 further characterized by said control means (38) including preamplifier means (50) for amplifying said detection signal.

10. An assembly as set forth in claim 9 further characterized by said control means (38) including processor means (52) for receiving said data signal to produce an output indicative of parameters of the solid and for controlling said driver means (44).

11. An assembly as set forth in claim 5 further characterized by said scanner means (40) including an array of detectors for detecting said reflected beam to produce said detection signal.

12. A method for measuring optical and thermal parameters of a sample, said method including the steps of; producing a thermal bump (20) on a sample, directing a probe laser beam (30) having a beam area greater than the test area toward the test area, detecting the reflected probe laser beam (31) reflected from the test area, measuring the interference pattern of the reflected probe laser beam (31) caused by the thermal bump (20).

13. A method as set forth in claim 12 further including producing the thermal bump by heating the test area by a heating laser beam directed perpendicular to the sample.

14. A method as set forth in claim 13 further including directing the probe laser beam at an angle less than 90° toward the test area.

15. A method as set forth in claim 14 further including scanning the reflected laser beam to measure the wave pattern of interference and producing a detection signal.

16. A method as set forth in claim 15 further including intensity modulating the heating laser beam and focusing the modulated beam to the test area.

17. A method as set forth in claim 16 further including synchronizing the detecting with the modulating.

* * * * *